United States Patent [19]

Go et al.

[11] Patent Number: 5,286,589
[45] Date of Patent: Feb. 15, 1994

[54] ELECTROPHOTOGRAPHIC PHOTOSENSITIVE MEMBER

[75] Inventors: Shintetsu Go; Kazushi Iuchi, both of Yokohama; Toshie Miyaji, Kawasaki; Hajime Miyazaki, Yokohama; Hideyuki Takai, Yokohama; Masakazu Matsumoto, Yokohama, all of Japan

[73] Assignee: Canon Kabushiki Kaisha, Tokyo, Japan

[21] Appl. No.: 975,137

[22] Filed: Nov. 12, 1992

Related U.S. Application Data

[63] Continuation of Ser. No. 766,976, Sep. 26, 1991, abandoned, which is a continuation of Ser. No. 488,732, Feb. 26, 1990, abandoned.

Foreign Application Priority Data

Feb. 27, 1989 [JP] Japan .................. 1-045712

[51] Int. Cl.$^5$ .................. G03G 5/06; G03G 5/047; G03G 15/22
[52] U.S. Cl. .................. 430/58; 430/59; 430/72; 430/73; 430/75; 430/76; 430/77; 430/78; 430/79; 430/900; 355/211
[58] Field of Search .................. 430/58, 59, 72, 73, 430/75, 76, 77, 78, 79, 900; 355/211

[56] References Cited

U.S. PATENT DOCUMENTS

| | | | |
|---|---|---|---|
| 3,041,165 | 6/1962 | Sus et al. | 430/76 X |
| 4,448,868 | 5/1984 | Suzuki et al. | 430/58 |
| 4,465,753 | 8/1984 | Tanaka et al. | 430/78 X |
| 4,529,678 | 7/1985 | Ohta | 430/59 X |
| 4,666,809 | 5/1987 | Matsumoto et al. | 430/76 |
| 4,798,777 | 1/1989 | Takiguchi et al. | 430/59 |
| 4,931,371 | 6/1990 | Matsumoto et al. | 430/59 |

FOREIGN PATENT DOCUMENTS 111249 6/1985 Japan .

*Primary Examiner*—Roland Martin
*Attorney, Agent, or Firm*—Fitzpatrick, Cella, Harper & Scinto

[57] ABSTRACT

An electrophotographic photosensitive member has a photosensitive layer on an electroconductive support. The photosensitive layer comprises a compound having a structure represented by the general formula (1) or (2) as a charge-generating material:

$$A_1 \!+\! \underset{\underset{A_2}{|}}{C} \!=\! N \!-\! A_3]_n \qquad (1)$$

$$A_3 \!+\! N \!=\! \underset{\underset{A_2}{|}}{C} \!-\! A_1]_n \qquad (2)$$

wherein $A_1$ and $A_3$ are respectively an alkyl radical, an aralkyl radical, an aromatic radical or a heterocyclic radical which may have a substituent; $A_2$ is hydrogen atom, or an alkyl radical, an aralkyl radical, an aromatic radical, or a heterocyclic radical which may have a substituent; $A_1$ and $A_2$ may be the same with or different from each other; $A_1$ and $A_2$ may be linked together to form a ring; and n is an integer of 1, 2, or 3.

13 Claims, 1 Drawing Sheet

ELECTROPHOTOGRAPHIC PHOTOSENSITIVE MEMBER

This application is a continuation of application Ser. No. 07/766,976 filed Sept. 26, 1991, now abandoned, which is a continuation of application Ser. No. 07/488,732 filed Feb. 26, 1990, now abandoned.

BACKGROUND OF THE INVENTION

1. Field of the Invention

The present invention relates to an electrophotographic photosensitive member. More particularly, the present invention relates to an electrophotographic photosensitive member superior in sensitivity and potential stability.

2. Related Background Art

Recent electrophotographic photosensitive members comprising an organic compound as a main constituent have various advantages such as superior film-forming property, non-pollution, ease of manufacture, and so on, as compared with inorganic type photosensitive members. In particular, some lamination type photosensitive members are practically used which includes a layer containing a material for generating electric charge on light irradiation (a charge-generating layer and a layer containing a material for transporting the generated charge (a charge-transporting layer) because of their higher sensitivity and high-charge stability. Photosensitive members employing an azo pigment which is a typical charge-generating material were disclosed in Japanese Patent Application Laid-open No. 59-33445 and No. 60-111249. Such photosensitive members employing the azo pigment as the charge-generating material are not always satisfactory in sensitivity, residual potential, or stability in repeated use, and are limited in the range of selection of the charge-transporting material, thus not satisfying extensive requirements for electrophotographic processes.

SUMMARY OF THE INVENTION

The present invention intends to provide an electrophotographic photosensitive member having a high sensitivity and high durability.

The present invention provides an electrophotographic photosensitive member having a photosensitive layer on an electroconductive support, the photosensitive layer comprising a compound represented by the general formula (1) or (2) as a charge-generating material:

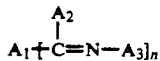  (1)

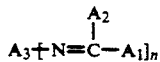  (2)

wherein $A_1$ and $A_3$ are respectively an alkyl radical, an aralkyl radical, an aromatic radical or a heterocyclic radical which may have a substituent; $A_2$ is hydrogen atom, or an alkyl radical, an aralkyl radical, an aromatic radical, or a heterocyclic radical which may have a substituent; $A_1$ and $A_2$ may be the same with or different from each other; $A_1$ and $A_2$ may be linked together to form a ring; and n is an integer of 1, 2, or 3.

DETAILED DESCRIPTION OF THE PREFERRED EMBODIMENT

Figure 1:
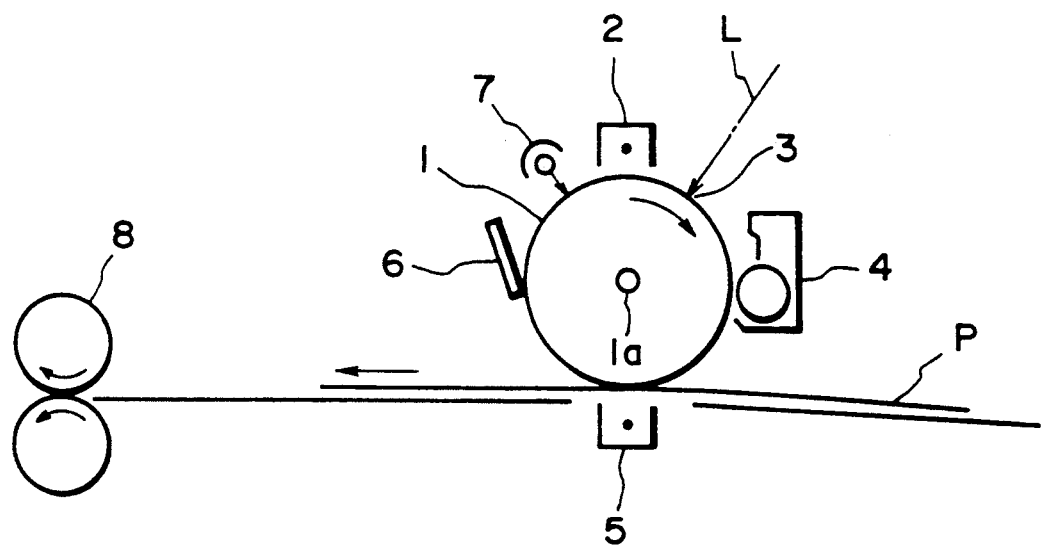
FIG. 1 illustrates an example of constitution of a usual transfer-type electrophotographic photosensitive member employing a drum-form photosensitive member.

For the radicals of $A_1$, $A_2$, and $A_3$ in the present invention, the alkyl radicals include methyl, ethyl, propyl, butyl, etc. The aralkyl radicals therefor include benzyl, phenethyl, naphthylmethyl, etc. The aromatic radicals therefor include aromatic monocyclic radicals and aromatic condensed polycyclic radicals of compounds such as benzene, naphthalene, anthracene, phenanthrene, pyrene, azulene, indene, fluorene, etc.; assembled ring radicals constituted by direct combination through a double bond or the like of two or more of the aforementioned aromatic monocyclic groups and aromatic condensed polycyclic radicals; aromatic ketone radicals such as benzophenone, fluorenone, benzanethrone, indanone, suberenone, etc., their sulfur derivative radicals (e.g., thiobenzophenone), and their dicyanomethylene derivative radicals; and aromatic quinone radicals of compounds such as benzoquinone, naphthoquinone, anthraquinone, phenanthrenequinone, pyrenequinone, etc., their sulfur derivative radicals, and their dicyanomethylene derivative radicals. The heterocyclic radicals therefor include heterocyclic monocyclic ring radicals and heterocyclic radicals condensed with a benzene ring or an aromatic condensed polycyclic group of a compound such as furan, thiophene, pyrrole, oxazole, thiazole, imidazole, pyrazole, pyridine, pyrazine, piperadine, benzofuran, benzothiophene, indole, benzoxazole, benzothiazole, dibenzofuran, dibenzothiophene, carbazole, phenazine, phenoxazine, phenothiazine, thianthrene, acridone, etc.; and assembled ring radicals constituted by direct combination through a double bond or the like of two or more of the aforementioned aromatic monocyclic and condensed polycyclic radicals. The assembled ring radicals may be constituted by direct combination of at least one of the heterocyclic monocyclic radicals and condensed heterocyclic radicals and at least one of the aromatic monocyclic radicals and aromatic condensed polycyclic radicals.

The substituents which may be attached to the alkyl radicals, the aralkyl radicals, or the heterocyclic radicals mentioned above include halogen substituents such as fluorine, chlorine, bromine, and iodine; alkyl radicals such as methyl, ethyl, propyl, butyl, etc.; alkoxy radicals such as methoxy, ethoxy, phenoxy, etc.; a nitro radical; a cyano radical: substituted amino radicals such as dimethylamino, dimethylamino, diphenylamino, dibenzylamino, morpholino, piperidino, pyrrolidino, etc.

In the general formulas (1) and (2), $A_1$ and $A_2$ may be the same with or different from each other, $A_1$ and $A_2$ may be linked together to form a ring, and n is an integer of 1, 2, or 3. Moreover, in the general formulas (1) and (2). when $A_1$ and $A_2$ are electron-donating moieties. $A_3$ is preferably an electron-accepting moiety, and when $A_1$ and $A_2$ are electron-accepting moieties, then $A_3$ is preferably an electron-donating moiety. In particular, excellent characteristics are achieved in the case where an electron-donating moiety is linked on the N side of the $>C=N-$ bond, and an electron-accepting moiety is linked on the C side thereof.

The electron-donating moiety includes aromatic monocyclic radicals and aromatic condensed polycyclic radicals of compounds such as benzene, naphthalene, anthracene, phenanthrene, indene, fluorene, etc. which have an electron-donating substituent, and pyrene etc. which may have an electron-donating substituent; electron-donating aromatic amine radicals of compounds such as triphenylamine, diphenylamine, diphenylmethylamine, etc. which may have an electron-donating substituent; electron-donating heterocyclic monocyclic radicals and electron-donating condensed heterocyclic radicals which are constituted by condensation with a benzene ring or an aromatic condensed polycyclic group of a compound such as furan, thiophene, pyrrole, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, phenothiazine, etc. which have an electron-donating substituent, and radicals of indole, carbazole, iminodibenzyl, tetrathiafulvalene, dibenzotetrathiafluvalene, etc. which may have an electron-donating substituent; and assembled ring radicals constituted by direct combination through a double bond or the like of two or more of the aforementioned monocyclic groups and condensed polycylic radicals.

The electron-donating substituent includes alkyl radicals such as methyl, ethyl, propyl, butyl, etc.; aryl radicals such as phenyl, naphthyl, etc.; aralkyl radicals such as benzyl, phenethyl, etc; alkoxy radicals such as methoxy, ethoxy, etc.: and substituted amino radicals such as dimethylamino, diphenylamino, morpholino, etc.

On the other hand, the electron-accepting moiety include electron-accepting aromatic monocyclic radicals and electron-accepting aromatic condensed polycyclic radicals of such as benzene, naphthalene, anthracene, phenanthrene, indene, fluorene, etc. which have an electron-accepting substituent; electron-accepting aromatic ketone radicals of such as benzophenone, fluorenone, benzanthrone, etc. which may have an electron-accepting substituent, and their dicyanomethylene derivative radicals; electron-accepting aromatic thioketone radicals; electron-accepting aromatic quinone radicals of compounds such as benzoquinone, naphthoquinone, anthraquinone, pyrenequinone, etc., and their dicyanomethylene derivative radicals; electron-accepting heterocyclic monocyclic radicals and electron-accepting condensed heterocyclic radicals which are constituted by condensation with a benzene ring or an aromatic condensed polycyclic group of a compound such as furan, thiophene, pyrrole, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, phenothiazine, etc. which have an electron-accepting substituent; and electron-accepting assembled ring radicals constituted by direct combination through a double bond or the like of two or more of the aforementioned aromatic monocyclic or condensed polycyclic radicals.

The electron-accepting substituent includes halogens such as fluorine, chlorine, bromine, and iodine a nitro radical: and a cyano radical.

In the present invention, the term "electron-donating radical" and "electron-accepting radical" mean a moiety exhibiting a negative value of Hammet's $\sigma$ constant, and a moiety exhibiting a positive value of Hammet's $\sigma$ constant, respectively.

As $A_2$, hydrogen is especially preferable from among the above-mentioned radicals.

In order to achieve spectrographic sensitivity of electrophotographic photosensitive member in a long wavelength region, the charge-generating material is required to exhibit absorption spectrum at the long wavelength region. Extension of a $\pi$-electron conjugation system, or increase of intermolecular interaction are known to give long-wavelength absorption. As to the substituent effect, it has been reported that substituted azobenzenes have stronger absorption at long wavelengths as the substituent has stronger electron-donating property, or as the substituent has a stronger electron-accepting property. This effect is considered to result from the intermolecular charge-transfer interaction through the azo group (—N=N—), namely a $\pi$-electron conjugation chain, of the azobenzene (J.Griffiths, "Colour and Construction of Organic Molecules", Academic Press London, 1976, and great increase of long wavelength absorption is expected to be given by combination of a strong electron-donating moiety and a strong electron-accepting moiety.

On the other hand, the improvement of charge carrier generation efficiency is required for improving sensitivity in electrophotographic photosensitive members. One factor relating to the charge carrier generation efficiency is a dissociation efficiency of the carrier. A local electric field, which is formed by ionically adsorbed gas or the like, is reported to have a great influence on the carrier dissociation efficiency in the case of phthalocyanine compounds (see, for example, Denki Shashin Gakkaishi (Journal of Electrophotographic Society) Vol.20, p.216, (1987)).

From the standpoint as described above, the photoconductive compounds of the present invention exhibits excellent characteristics, in particular in the case where the electron-donating moiety and the electron-accepting moiety interact mutually through the $>C=N-$ bond, and further the electron-donating moiety and the electron-accepting moiety interact mutually between molecules in a crystalline state to cause charge transfer.

Typical examples of the compounds represented by the general formulas (1) and (2) are shown below.

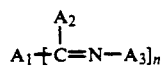
(1)
(n = 1, 2, or 3)
| Compound No. | Structural formula |
|---|---|
| A-1 | 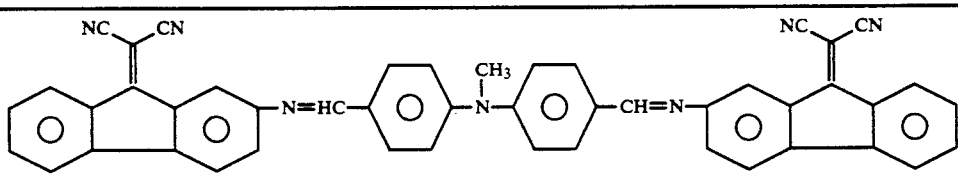 |
| A-2 | 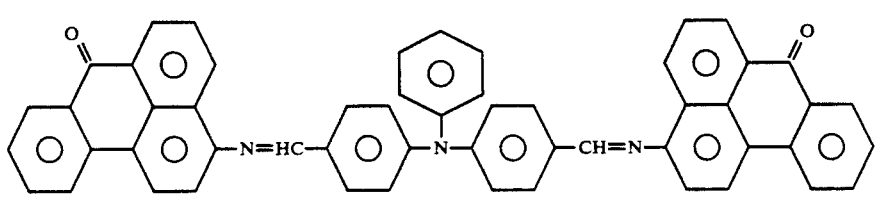 |
| A-3 | 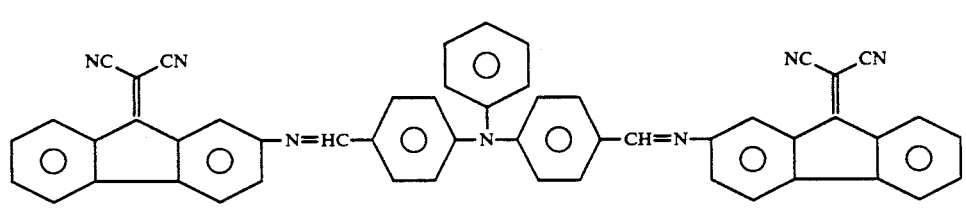 |
| A-4 | 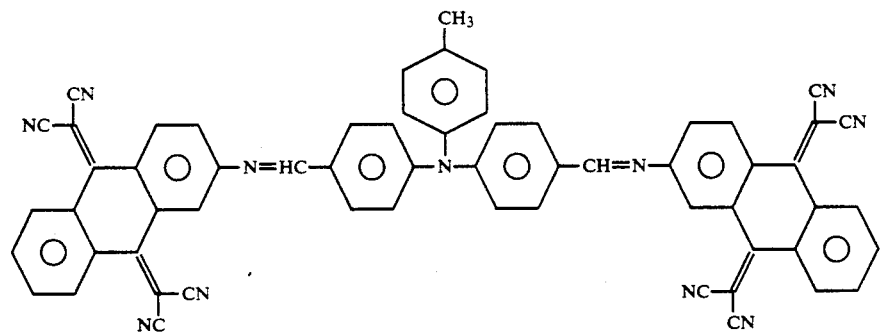 |
| A-5 | 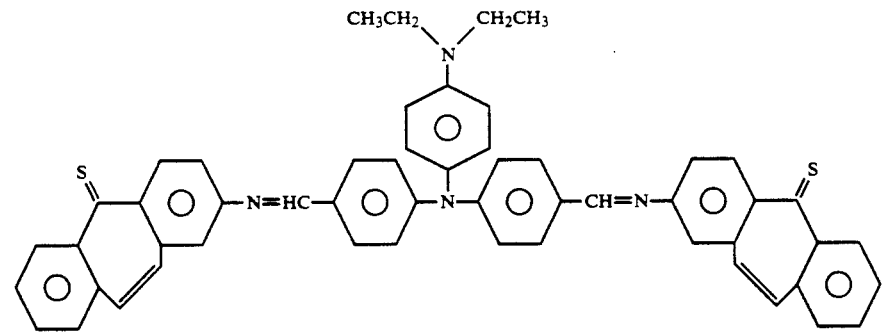 |
| A-6 | 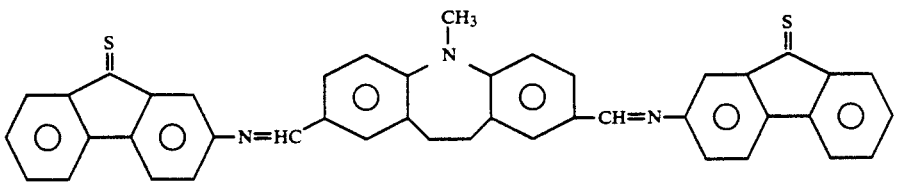 |

-continued
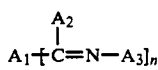
(n = 1, 2, or 3)
| Compound No. | Structural formula |
|---|---|
| A-7 | 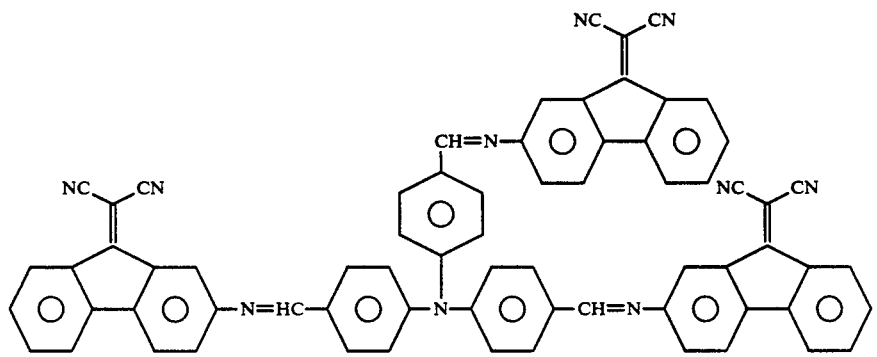 |
| A-8 | 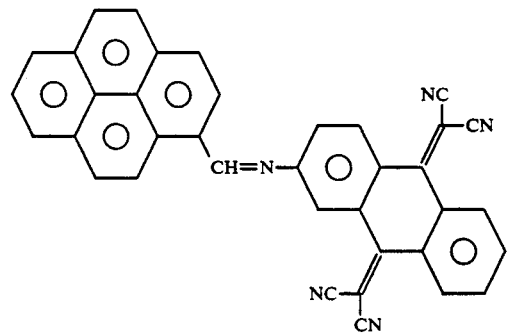 |
| A-9 | 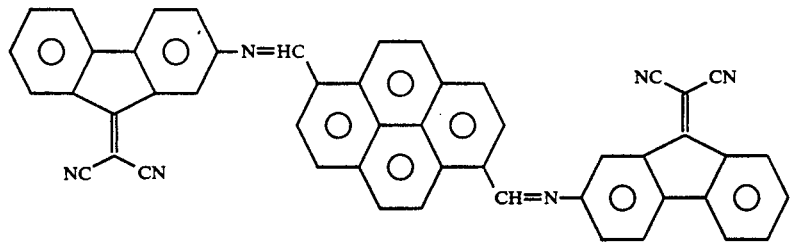 |
| A-10 | 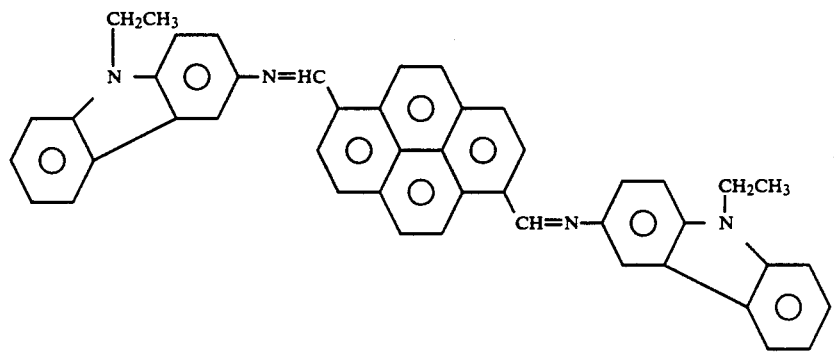 |

-continued
$$A_1\text{−}[C(A_2)\text{=}N\text{−}A_3]_n \quad (1)$$
(n = 1, 2, or 3)
| Compound No. | Structural formula |
|---|---|
| A-11 | 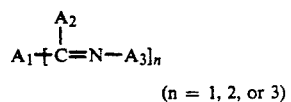 |
| A-12 | |
| A-13 | |
| A-14 | |
| A-15 | |

-continued
$$A_1\text{-}[C(A_2)=N\text{-}A_3]_n \quad (1)$$
(n = 1, 2, or 3)
| Compound No. | Structural formula |
|---|---|
| A-16 |  |
| A-17 | |
| A-18 | |
| A-19 | |
| A-20 | |

-continued
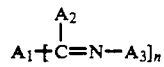
(n = 1, 2, or 3)
| Compound No. | Structural formula |
|---|---|
| A-21 | 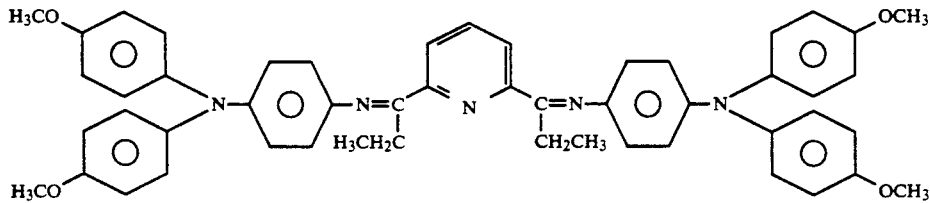 |

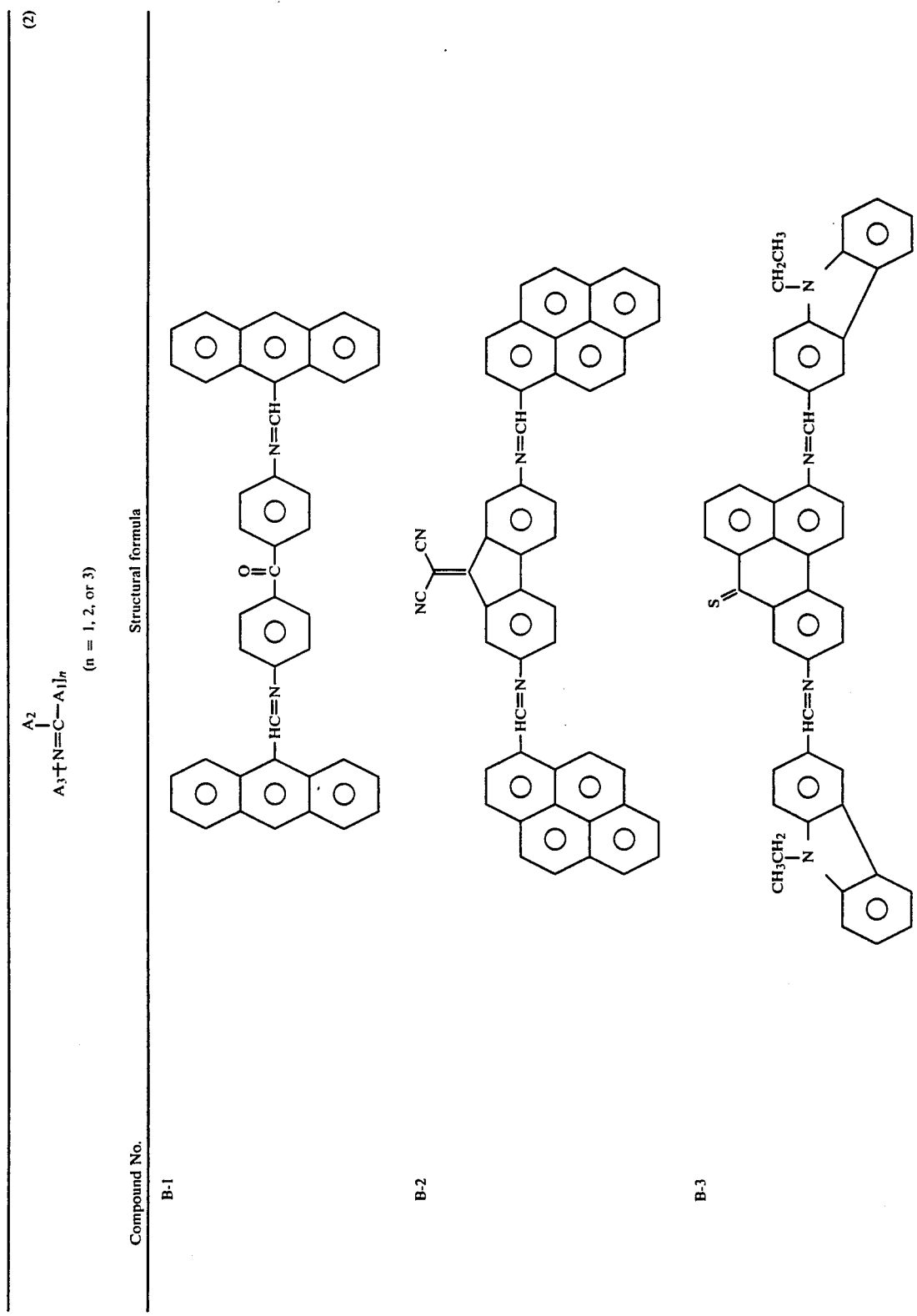

-continued
$$A_1 \{ N=C-A_1 \}_n \overset{A_2}{|}$$
(n = 1, 2, or 3)
| Compound No. | Structural formula |
|---|---|
| B-4 | 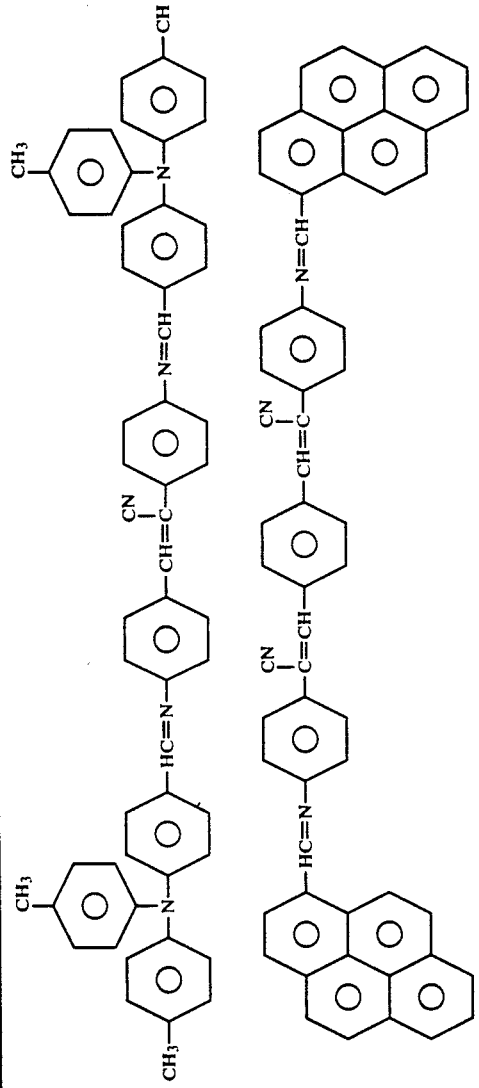 |
| B-5 | 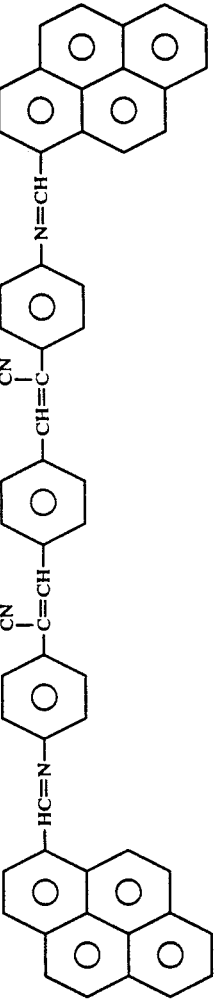 |
| B-6 | 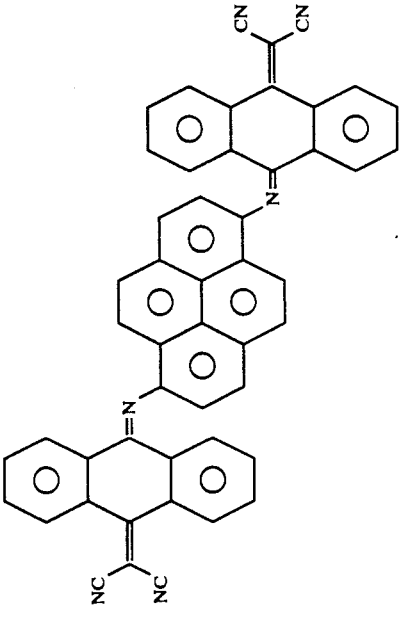 |

-continued $$A_3 \!\!\!-\!\!\!\!\begin{array}{c} A_2 \\ | \\ N\!=\!C\!-\!A_1 \end{array}\!\!\!\!\Big)_n \quad (2)$$

(n = 1, 2, or 3)

| Compound No. | Structural formula |
|---|---|
| B-7 | |
| B-8 | |
| B-9 | |
| B-10 | |

-continued
$$A_3 + N=C-A_1]_n \quad (2)$$
$$\overset{|}{A_2}$$
(n = 1, 2, or 3)
| Compound No. | Structural formula |
|---|---|
| B-11 |  |
| B-12 | |
| B-13 | |

-continued
$$\underset{A_3 \vdash N=C-A_1]_n}{\overset{A_2}{|}}$$ (2)
(n = 1, 2, or 3)
| Compound No. | Structural formula |
|---|---|
| B-14 | 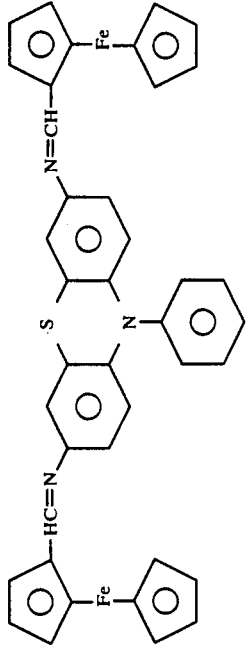 |
| B-15 | 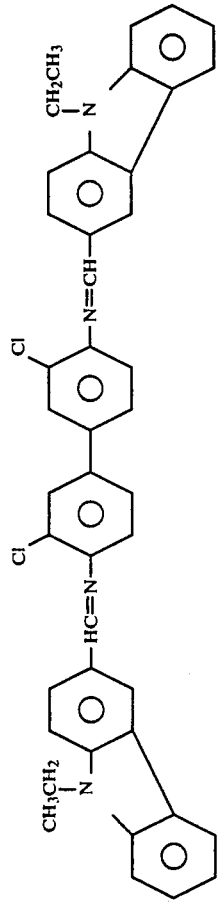 |
| B-16 | 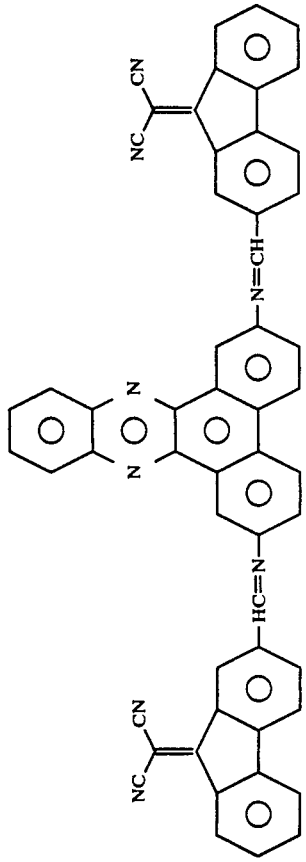 |

-continued
$$A_3 \left[ N = \overset{A_2}{\underset{|}{C}} - A_1 \right]_n \quad (2)$$
(n = 1, 2, or 3)
| Compound No. | Structural formula |
|---|---|
| B-17 |  |
| B-18 | 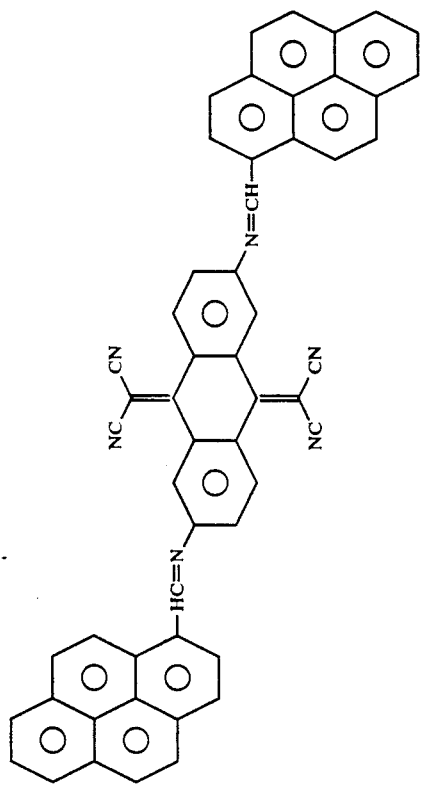 |
| B-19 | 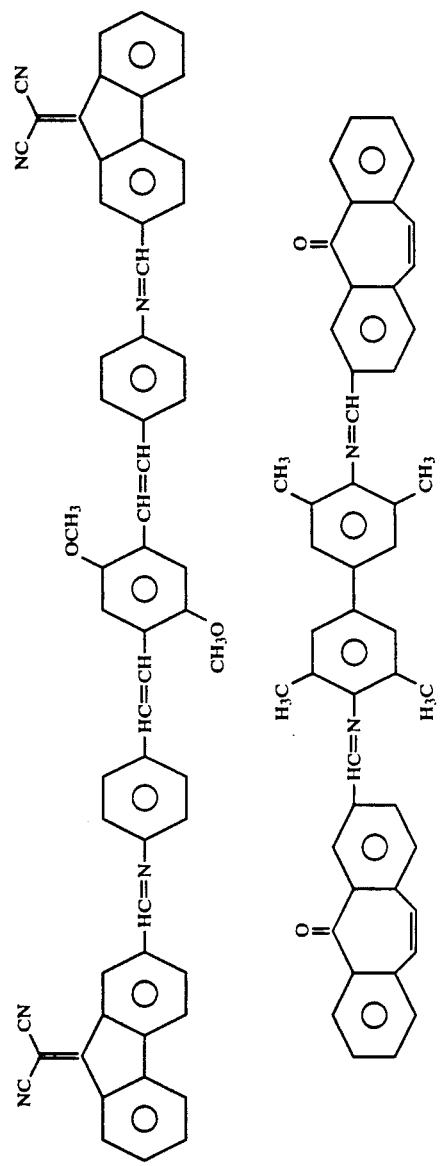 |

-continued
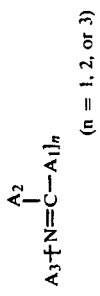
(2)
(n = 1, 2, or 3)
| Compound No. | Structural formula |
|---|---|
| B-20 | 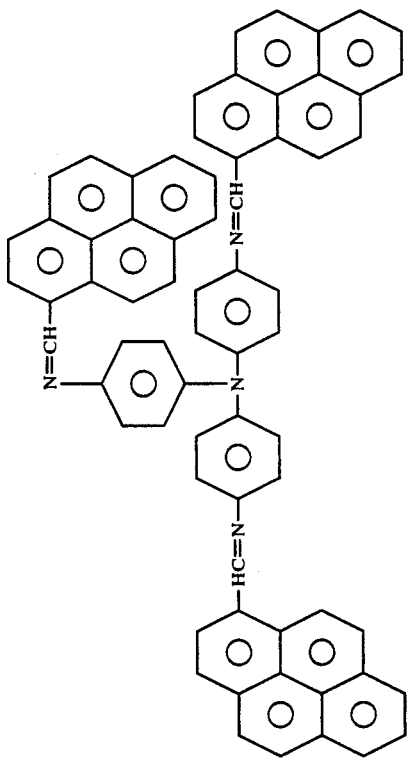 |
| B-21 | 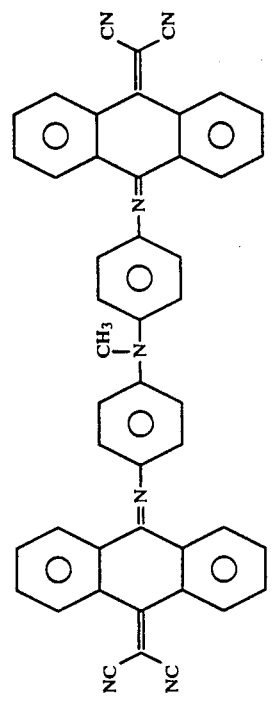 |

-continued
$$A_3\{N=C-A_1\}_n \quad \overset{A_2}{|} \quad (2)$$
(n = 1, 2, or 3)
| Compound No. | Structural formula |
|---|---|
| B-22 | 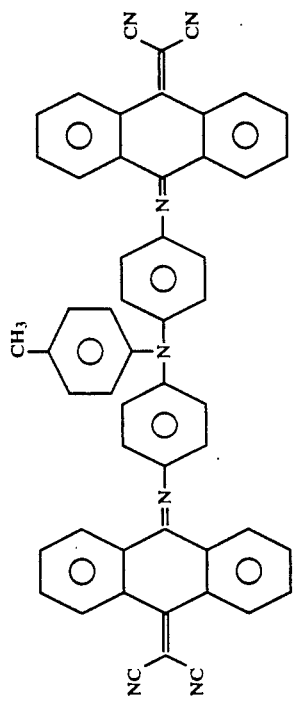 |
| B-23 | 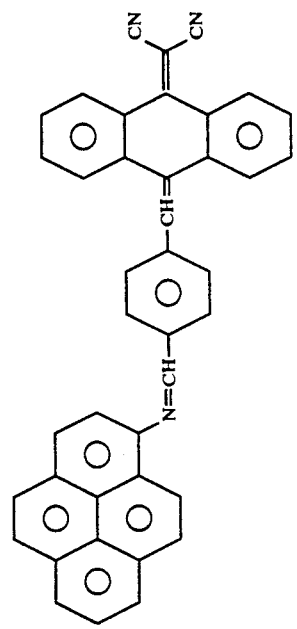 |

-continued
$$A_3 \text{+} N = C - A_1]_n \quad (2)$$
$$\overset{A_2}{|}$$
(n = 1, 2, or 3)
| Compound No. | Structural formula |
|---|---|
| B-24 | 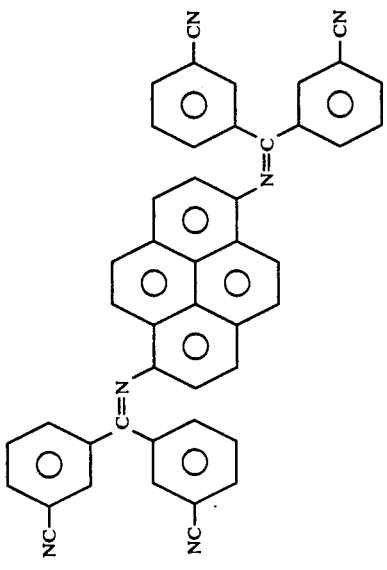 |
| B-25 | 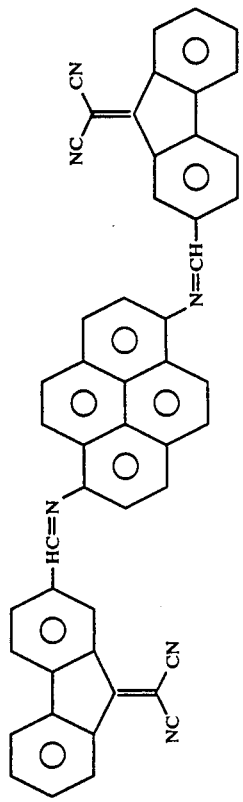 |

-continued
$$A_1 \!\!+\!\! N\!\!=\!\!\overset{A_2}{\overset{|}{C}}\!\!-\!\!A_1]_n \quad (2)$$
(n = 1, 2, or 3)
| Compound No. | Structural formula |
|---|---|
| B-26 | 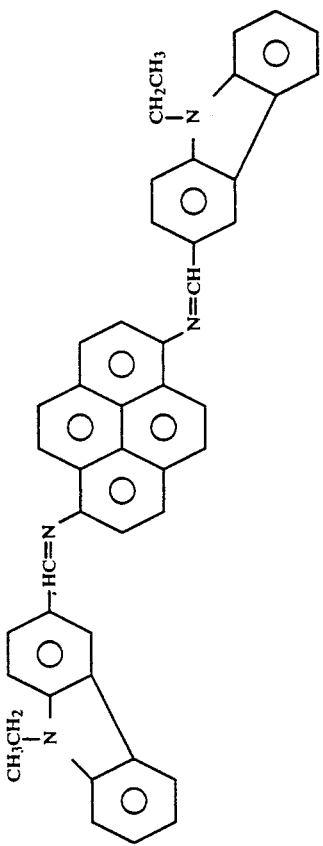 |
| B-27 | 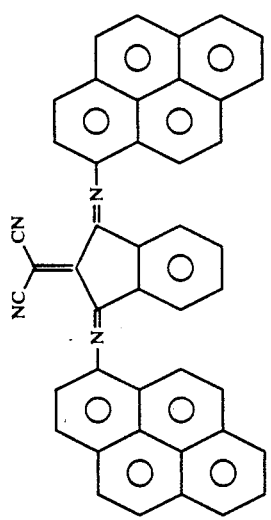 |
| B-28 | 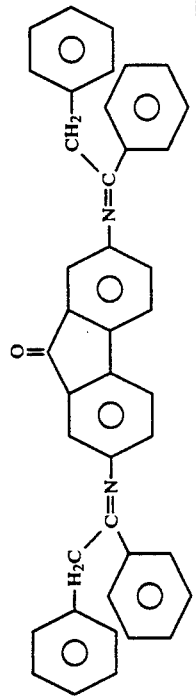 |

The compounds represented by the general formulas (1) and (2) are synthesized readily by the dehydrating-condensation reaction of a corresponding aromatic amine and an aromatic aldehyde or an aromatic ketone in the presence of a basic catalyst as shown in the reaction formula below.

Acid or base

Ar—CHO+Ar'—NH₂→Ar—CH=N—Ar'

The electrophotographic photosensitive member of the present invention is provided on an electroconductive support& with a photosensitive layer containing the compound represented by the general formula (1) or (2) as the charge-generating material.

The photosensitive layer may be in any form. A function-separating type of photosensitive layer is particularly preferable which is constituted of a charge-generating layer containing the compound represented by the general formula (1) or (2), and a charge-transporting layer containing a charge-transporting material laminated thereon.

In this case, the charge-generating layer is formed by applying on an electroconductive supporter a coating solution containing a binder resin dispersed in a suitable solvent by a known method. The film is desirably made thin, for example, to a thickness of 5 μm or less, preferably from 0.01 μm to 1 μm.

The binder resin employed therefor may be selected from broad range of insulative resins and organic photoconductive resins. The preferable resins include polyvinyl butyrals, polyvinyl benzals, polyarylates, polycarbonates, polyesters, phenoxy resins, cellulose resins, acrylic resins, urethane resins, etc. The content thereof in the charge-generating layer is not more than 80% by weight, preferably not more than 40% by weight.

The solvent for the binder resin is preferably selected from solvents which dissolve the aforementioned resin but do not dissolve the charge-transporting layer or the subbing layer mentioned below. Specifically the solvent includes ethers such as tetrahydrofuran, 1,4-dioxane, etc.; ketones such as cyclohexanone, methyl ethyl ketone, etc.; amides such as N,N-dimethylformamide, etc.; esters such as methyl acetate, ethyl acetate, etc.; aromatic solvents such as toluene, xylene, monochlorobenzene, etc.; alcohols such as methanol, ethanol, 2-propanol, etc.; and aliphatic halogenated hydrocarbons such as chloroform, methylene chloride, etc.

The charge-transporting layer, which is laminated on the upper side or the lower side of the charge-generating layer, functions to receive charge carriers from the charge-generating layer in an electric field, and transport the carriers to the surface. The charge-transporting layer is formed by applying a charge-transporting material, with a suitable binder if necessary, dissolved in a solvent. Generally the thickness of the film is preferably in the range of from 5 μm to 40 μm, more preferably from 15 μm to 30 μm.

The charge-transporting material includes electron-transporting materials and positive-hole-transporting materials. Examples of the electron-transporting materials are electron-attracting materials such as 2,4,7-trinitrofluorenone, 2,4,5,7-tetranitrofluorenone, chloranil, tetracyanoquinodimethane, etc. and polymerized products of these electron-attracting materials.

The examples of the positive-hole-transporting materials are aromatic polycyclic compounds such as pyrene, anthracenne, etc.; heterocyclic compounds such as carbazole, indole, imidazole, oxazole, thiazole, oxadiazole, pyrazole, pyrazoline, thiadiazole, triazole, etc.; hydrazone compounds such as p-diethylaminobenzaldehyde-N,N-diphenylhydrazone, N,N-diphenylhydrazino-3-methylidene-9-ethylcarbazole, etc.; styryl compounds such as α-phenyl-4'-N,N-diphenylaminostylbene, 5-[4-(di-ptolylamino)benzylidene]-5H-dibenzo[a,d]cycloheptene, etc.; benzidine compounds; triarylmethane compounds triphenyl amines; polymers such as poly-N-vinylcarbazole, polyvinylanthracene, etc. having in the main chain or a side chain radicals from the aforementioned compounds.

Inorganic materials such as selenium, selenium-tellurium, amorphous silicon, etc. may also be used in addition to the organic charge-transporting materials.

The above-mentioned charge-transporting materials may be used singly or in combination of two or more materials.

When a charge-transporting material having no film-forming property is used, a suitable binder may be used with it. Specific examples of the binders includes insulative resins such as acrylic resins, polyarylates, polyesters, polycarbonates, polystyrenes, acrylnitrile-styrene copolymers, polysulfones, polyacrylamides, polyamides, chlorinated rubbers, etc.; organic photoconductive polymers such as poly-N-vinylcarbazole, polyvinylanthracene, etc; and the like.

Useful materials for the electroconductive support include aluminum, aluminum alloys, copper, zinc, stainless steel, titanium, etc. In addition thereto, also useful are plastics coated with a film of these metals formed by vacuum vapor deposition; plastic or metal supporters coated with electroconductive particles (e.g., carbon black, silver particles etc.) together with a binder; plastics or paper impregnated with electroconductive particles; and the like.

The electroconductive support may either be in a form of sheet or in a form of a drum.

Between the electroconductive supporter and the photosensitive layer, a subbing layer may be provided which has a barrier function and an adhesion function. The subbing layer may have a thickness of 5 μm or less, preferably from 0.1 μm to 3 μm. The subbing layer may be formed from a material such as casein, polyvinyl alcohol, nitrocellulose, polyamides (nylon 6, nylon 66, nylon 610, copolymer nylon, N-alkoxymethylated nylon, etc), polyurethane, aluminum oxide, etc.

On the photosensitive layer, there may be laminated a resin layer, or a resin layer containing electroconductive material dispersed therein, as a protecting layer.

Another specific example of the present invention is an eleotrophotographic photosensitive member containing the above-mentioned compound and a charge transporting material in the same layer. In this example, a charge transfer complex composed of poly-N-vinylcarbazole and trinitrofluorenone may be used as the charge transporting material.

The electrophotographic photosensitive member of this example may be formed by applying a liquid comprising the above-mentioned compound and the charge transporting material dispersed in a suitable resin solution, and drying it.

In any of the electrophotographic photosensitive members, the employed compound represented by the general formula (1) or (2) may either be crystalline or non-crystalline, and may be employed in combination of two or more compounds represented by the general formula (1) or (2), or in combination with a known charge-generating material.

The electrophotographic photosensitive member of the present invention is useful not only for electrophotographic copying machines but is also widely useful in electrophotography application field such as laser beam printers, CRT printers, LED printers, liquid crystal printers, laser engraving, etc.

FIG. 1 illustrates an outline of constitution of a usual transfer-type electrophotographic photosensitive member employing a photosensitive member in a drum form.

In the figure, the numeral 1 denotes a drum type photosensitive member as an image bearer, which is driven to rotate around the axis 1a in the arrow direction at a predetermined peripheral speed. The photosensitive member 1 is electrostatically charged uniformly to a predetermined positive or negative potential at the peripheral surface with a charging means 2 while rotating. Then it is exposed to an image-projecting light L (e.g., slit projection, laser beam scanning projection, etc.) at the light exposure portion 3 from an image-projecting means not shown in the figure. Thus an electrostatic latent image is successively formed on the peripheral surface of the photosensitive member.

The electrostatic latent image is subsequently developed by use of a toner with the image-developing means 4. The developed toner image is sequentially transferred by a transfer means 5 onto the transfer-receiving medium P which is fed from a paper feed section (no& shown) between the photosensitive member 1 and the transfer means 5 synchronously with the rotation of the photosensitive member 1.

The transfer-receiving medium P having received the transferred image is separated from the photosensitive member surface and introduced to the image fixing means 8 to have the image fixed and to be printed out of the machine as a duplicate (a copied material).

After the image transfer, the surface of the photosensitive member 1 is cleaned with a cleaning means 6 to remove the residual toner, and is repeatedly used for image formation.

As the charging means 2 for uniformly charging the photosensitive member 1 eleotrostatically, corona charging apparatus are generally and widely used. As the transferring apparatus, corona transferring means are also generally and widely used. Plural means from among the constitutional elements, such as a photosensitive member, a developing means, and be cleaning means, may be integrated into one apparatus unit, which may be made freely mountable and dismountable. For example, the photosensitive member 1 and the cleaning means 6 are integrated into one apparatus unit and are made to be freely mountable and dismountable by use of a guide means such as a rail provided in the body of the apparatus. The apparatus unit may be constituted to incorporate a charging means and/or a developing means.

EXAMPLES 1-47

On an aluminum substrate plate, a subbing layer having a dried film thickness of 1 μm has provided by applying with a Meyer bar a solution of 5 g of a methoxymethylated nylon resin (number-average molecular weight: 32000) end 10 g of an alcohol-soluble copolymer nylon resin (number-average molecular weight: 29000) in 95 g of methanol.

Separately, 5 g of Compound A-1 shown before was added into a solution of 2 g of a butyral resin (butyrala-tion degree: 63 mole %) in 95 g cyclohexanone and was dispersed with a sand mill for 20 minutes. This dispersion was applied on the preliminarily formed subbing layer to give a dried thickness of 0.2 μm with a Meyer bar, to form a charge-generating layer.

5 g of the hydrazone compound represented the formula below:

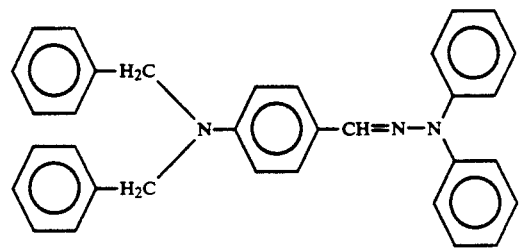

and 5 g of polymethyl methacrylate (number-average molecular weight: 100000) were dissolved in 40 g of monochlorobenzene. The solution was applied on the charge-generating layer prepared above with a Meyer bar and dried to form a charge-transporting layer having a thickness of 20 μm, thus providing a photosensitive member of Example 1.

The photosensitive member of Examples 2 to 47 were prepared in the same manner as described above except that compounds other than compound A-1, which are shown in Table 1, were employed.

The electrophotographic photosensitive members prepared thus were evaluated for charging characteristics with an electrostatic copying paper tester (Model SP-428, made by Kawaguchi Denki K.K.), where the photosensitive member was negatively charged by corona discharge of $-5$ KV, left standing for 1 second in the dark, and exposed to light of 10 lux with a halogen lamp. The evaluation of the charging characteristics were performed by measuring the surface potentials ($V_O$) and the amounts of exposure ($E_{\frac{1}{2}}$) required for decreasing by half the surface potential after left standing in the dark.

The results are shown in Table 1 and Table 2.

TABLE 1

| Example No. | Compound No. | $V_O(-V)$ | $E_{\frac{1}{2}}$ (lux · sec) |
|---|---|---|---|
| 1 | A-1 | 700 | 3.2 |
| 2 | A-2 | 680 | 3.6 |
| 3 | A-3 | 695 | 2.5 |
| 4 | A-4 | 705 | 2.6 |
| 5 | A-5 | 680 | 4.1 |
| 6 | A-6 | 690 | 3.8 |
| 7 | A-7 | 695 | 3.2 |
| 8 | A-8 | 700 | 2.6 |
| 9 | A-9 | 710 | 2.6 |
| 10 | A-10 | 700 | 6.9 |
| 11 | A-11 | 695 | 4.5 |
| 12 | A-12 | 680 | 5.1 |
| 13 | A-13 | 705 | 3.8 |
| 14 | A-14 | 695 | 3.6 |
| 15 | A-15 | 710 | 3.0 |
| 16 | A-16 | 715 | 2.8 |
| 17 | A-17 | 710 | 2.4 |
| 18 | A-18 | 700 | 3.8 |
| 19 | A-19 | 710 | 3.1 |
| 20 | A-20 | 695 | 4.3 |

TABLE 2

| Example No. | Compound No. | $V_O(-V)$ | $E_{\frac{1}{2}}$ (lux · sec) |
|---|---|---|---|
| 21 | B-1 | 695 | 4.1 |
| 22 | B-2 | 710 | 2.1 |
| 23 | B-3 | 705 | 3.2 |
| 24 | B-4 | 715 | 2.8 |
| 25 | B-5 | 700 | 2.6 |
| 26 | B-6 | 700 | 2.0 |
| 27 | B-7 | 690 | 3.2 |
| 28 | B-8 | 685 | 4.7 |
| 29 | B-9 | 700 | 3.8 |
| 30 | B-10 | 675 | 5.0 |
| 31 | B-11 | 680 | 4.9 |
| 32 | B-12 | 690 | 5.9 |
| 33 | B-13 | 700 | 3.7 |
| 34 | B-14 | 695 | 4.8 |
| 35 | B-15 | 705 | 3.4 |
| 36 | B-16 | 710 | 2.9 |
| 37 | B-17 | 705 | 2.6 |
| 38 | B-18 | 690 | 4.0 |
| 39 | B-19 | 695 | 5.9 |
| 40 | B-20 | 705 | 3.6 |
| 41 | B-21 | 710 | 2.8 |
| 42 | B-22 | 715 | 2.9 |
| 43 | B-23 | 700 | 3.1 |
| 44 | B-24 | 695 | 3.7 |
| 45 | B-25 | 700 | 2.0 |
| 46 | B-26 | 705 | 7.2 |
| 47 | B-27 | 705 | 2.9 |

EXAMPLES 48–53

The electrophotographic photosensitive members prepared in Examples 4, 9, 17, 26, 37, and 45 were charged to $-700$ V, and the amounts of light exposure ($E_{\frac{1}{2}}$: $\mu J/cm^2$) to reduce the potential by half were measured with the apparatus used in Example 1. The light source used was an aluminum/pallium/arsine semiconductor laser (oscillation wavelength: 780 nm). The results are shown in Table 3.

TABLE 3

| Example No. | Compound No. | $E_{\frac{1}{2}}$ ($\mu J/cm^2$) |
|---|---|---|
| 48 | A-4 | 0.83 |
| 49 | A-9 | 0.85 |
| 50 | A-17 | 0.77 |
| 51 | B-6 | 0.68 |
| 52 | B-17 | 0.90 |
| 53 | B-25 | 0.71 |

These results show that the electrophotographic photosensitive members of the present invention have sufficient sensitivity also in the wavelength region of semiconductor laser oscillation.

EXAMPLES 54–56

The electrophotographic photosensitive member prepared in Example 3 was attached to a cylinder of an electrophotographic copying machine equipped with a $-6.5$ KV corona charger, an optical exposing system, image developer, a transfer charger, a charge-eliminating optical exposing system, and a cleaner.

The dark potential ($V_D$) and the light potential ($V_L$) at the initial stage were set at about $-300$ V and $-200$ V, respectively. After repeatedly used 5000 times, the dark potential and the light potential were measured.

The evaluation was also conducted in the same manner for the photosensitive members prepared in Examples 22, and 45. The results are shown in Table 4.

TABLE 4

| Example No. | Compound No. | Initial | | After 5000 repetitions | |
|---|---|---|---|---|---|
| | | $V_D(-V)$ | $V_L(-V)$ | $V_D(-V)$ | $V_L(-V)$ |
| 54 | A-3 | 700 | 195 | 690 | 205 |
| 55 | B-2 | 705 | 200 | 685 | 215 |
| 56 | B-25 | 700 | 200 | 685 | 210 |

EXAMPLE 57

On an aluminum surface of an aluminum-vapor-deposited polyethylene terephthalate film, a subbing layer of polyvinyl alcohol having a film thickness of 0.5 $\mu m$ was formed. Thereon, the compound dispersion employed in Example 3 was applied with a Meyer bar and dried to form the charge-generating layer of 0.2 $\mu m$ thick.

The styryl compound (5) represented by the formula below:

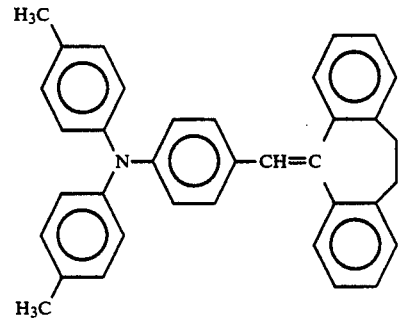

and 5 g of a polycarbonate resin (number average molecular weight: 55000) were dissolved in 40 g of tetrahydrofuran. This solution was applied on the charge-generating layer prepared above and dried to form a charge-transporting layer of 20 $\mu m$ thick. The photosensitive member thus prepared was tested for charging characteristics and durability in the same manner as in Example 1 and Example 52.

The results are shown below. The negative sign for the variation of the potential ($\Delta V$) means the decrease of the absolute value of the potential, and the positive sign means the increase thereof.

| $V_O$ | 705 ($-$V) | $E_{\frac{1}{2}}$ | 2.1 (lux · sec) |
|---|---|---|---|
| $\Delta V_D$ | 10 (V) | $\Delta V_L$ | 10 (V) |

EXAMPLE 58

A photosensitive member was prepared by applying the charge-generating layer and the charge-transporting layer of Example 57 in the reverse order. The photosensitive member was evaluated for charging characteristics in the same manner as in Example 1, provided that the charging was made positive.

| $V_O$ | 690 (+V) | $E_{\frac{1}{2}}$ | 3.5 (lux · sec) |
|---|---|---|---|

EXAMPLE 59

On the charge-generating layer prepared in Example 57, a solution of 5 g of 2,4,7-trinitro-9-fluorenone and 5 g of poly-4,4'-dioxydiphenyl-2,2'-propane carbonate (molecular weight: 300000) in 50 g of tetrahydrofuran was applied with a Meyer bar and dried to form a charge-transporting layer of 18 μm thick.

The electrophotographic photosensitive member prepared thus was evaluated for charging characteristics in the same manner as in Example 1, provided that the charging was made positive.

| $V_O$ | 680 (+V) | $E_{\frac{1}{2}}$ | 3.9 (lux · sec) |
|---|---|---|---|

EXAMPLE 60

Using a paint shaker, 0.5 g of the compound used in Example 3 was shaken with 9.5 g of cyclohexanone for 5 hours to disperse the compound. Thereto a solution of 5 g of the charge-transporting material employed in Example 1 and 5 g of a polycarbonate resin in 40 g of tetrahydrofuran was added, and the mixture was shaken for further 1 hour. The coating liquid thus prepared was applied and dried on an aluminum substrate plate by means of a Meyer bar to form a photosensitive layer of 20 μm thick.

The electrophotographic photosensitive member prepared thus was evaluated for charging characteristics in the same manner as in Example 1 provided that the charging was made positive.

| $V_O$ | 690 (+V) | $E_{\frac{1}{2}}$ | 4.6 (lux · sec) |
|---|---|---|---|

What is claimed is:

1. An electrophotographic photosensitive member having a photosensitive layer on an electroconductive support, said photosensitive layer comprising a laminated structure of a charge-generating layer on the electroconductive support and a charge-transporting layer on the charge-generating layer, wherein said charge generating layer contains a dispersed compound having a structure represented by the general formula (1) or (2) as a charge-generating material:

(1)

(2)

wherein $A_1$ and $A_3$ are respectively an aromatic radical or an aromatic heterocyclic radical; wherein when $A_3$ is an electron-accepting moiety, then $A_1$ is an electron-donating moiety and when $A_3$ is an electron-donating moiety, then $A_1$ is an electron-accepting moiety; $A_2$ is hydrogen atom and n is an integer of 1, 2, or 3.

2. The electrophotographic photosensitive member of claim 1, wherein the aromatic radical is at least one selected from the group consisting of aromatic monocyclic radicals, aromatic condensed polycyclic radicals, assembled ring radicals constituted by direct combination of two or more of the aromatic monocyclic radicals and aromatic condensed polycyclic radicals, aromatic ketone radicals, sulfur derivatives of the aromatic ketone radicals, dicyanomethylene derivatives of the aromatic ketone radicals, aromatic quinone radicals, sulfur derivatives of the aromatic quinone radicals, and dicyanomethylene derivatives of aromatic quinone radicals.

3. The electrophotographic photosensitive member of claim 1, wherein the heterocyclic ring radical is at least one selected from the group consisting of heterocyclic monocyclic ring radicals, condensed heterocyclic radicals constituted by condensation with a benzene ring or an aromatic condensed polycyclic group, and assembled ring radicals constituted by direct combination of two or more of the heterocyclic monocyclic radicals and condensed heterocyclic radicals, or by direct combination of at least one of the heterocyclic monocyclic radicals and condensed heterocyclic radicals and at least one of the aromatic monocyclic radicals and aromatic condensed polycyclic radicals.

4. The electrophotographic photosensitive member of claim 1, wherein the electron-donating moiety is linked on the N side of the >C=N— bond, and an electron-accepting moiety is bonded on the C side thereof in the general formulas (1) and (2).

5. The electrophotographic photosensitive member of claim 1, wherein the electron-donating moiety is at least one selected from the group consisting of aromatic monocyclic radicals, aromatic condensed polycyclic radicals, and assembled ring radicals constituted by direct combination of two or more of the aromatic monocyclic radicals and aromatic condensed polycyclic radicals, which may have an electron-donating substituent; aromatic amine radicals which may have an electron-donating substituent; heterocyclic monocyclic radicals which may have an electron-donating substituent; condensed heterocyclic radicals constituted by condensing the heterocyclic radicals with a benzene ring or an aromatic condensed polycyclic group; and assembled ring radicals constituted by direct combination of one or two of the heterocyclic monocyclic groups or condensed heterocyclic groups.

6. The electrophotographic photosensitive member of claim 5, wherein the electron-donating moiety is at least one selected from the group consisting of aromatic monocyclic radicals, aromatic condensed polycyclic radicals, and assembled ring radicals constituted by direct combination of two or more of the aromatic monocyclic radicals and aromatic condensed polycyclic radicals, which may have an electron donating substituent; aromatic amine radicals which may have an electron-donating substituent; heterocyclic monocyclic radicals which may have an electron-donating substituent; a condensed heterocyclic radicals constituted by condensing the heterocyclic radicals with a benzene ring or an aromatic condensed polycyclic group; and assembled ring radicals constituted by direct combination of one or two of the heterocyclic monocyclic groups and condensed heterocyclic groups.

7. The electrophotographic photosensitive member of claim 5, wherein the electron-donating moiety is selected from the group consisting of benzene, naphthalene, anthracene, phenanthrene, indene and fluorene which have an electron-donating substituent; pyrene which may have an electron-donating substituent; assembled ring radicals constituted by direct combination of two or more thereof; triphenylamine, diphenylamine, diphenylmethylamine which may have an electron-donating substituent: furan, thiophene, pyrrole, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, phenothiazine which have an electron-donating substituent; and indole, carbazole, iminodibenzyl, tetrathiafulvalene, dibenzotetrathiafulvalene which may have an electron-donating substituent; condensed heterocyclic radicals which are constituted by condensation of the heterocyclic ring with a benzene ring or an aromatic condensed polycyclic ring; end assembled ring radicals constituted by direct combination of two or more of the heterocyclic monocyclic radicals and the condensed heterocyclic groups.

8. The electrophotographic photosensitive member of claim 1, wherein the electron-accepting moiety is at least one selected from the group consisting of aromatic monocyclic radicals, aromatic condensed polycyclic radicals, and assembled ring radicals constituted by direct combination of two or more of the monocyclic radicals and condensed polycyclic radicals which have an electron-accepting substituent; aromatic ketone radicals and dicyanomethylene derivative radicals thereof, aromatic thioketone radicals, and aromatic quinone radicals and dicyanomethylene derivative radicals thereof, which may have an electron-accepting substituent; heterocyclic monocyclic radicals, condensed heterocyclic radicals which are constituted by condensation with a benzene ring or an aromatic condensed polycyclic radical, which have an electron-accepting substituent; and assembled ring radicals constituted by direct combination of two or more of the heterocyclic monocyclic groups and condensed heterocyclic polycyclic groups.

9. The electrophotographic photosensitive member of claim 8, wherein the electron-accepting moiety is at least one selected from the group of aromatic ketone radicals and dicyanomethylene derivative radicals thereof, aromatic thioketone radicals, and aromatic quinone radicals and dicyanomethylene derivative radicals thereof, which may have an electron-accepting substituent.

10. The electrophotographic photosensitive member of claim 8, wherein the electron-accepting moiety is at least one selected from the group consisting of benzene, naphthalene, anthracene, phenanthrene, indene, and fluorene which have an electron-accepting substituent and assembled ring radicals constituted by direct combination of one or two of the monocyclic group and condensed polycyclic groups; benzophenone, fluorenone, and benzanthrone which may have an electron-accepting substituent, and dicyanomethylene derivative radicals thereof; benzoquinone, naphthoquinone, anthraquinone, and pyrenequinone, and dicyanomethylene derivative radicals thereof; furan, thiophene, pyrrole, oxazole, thiazole, imidazole, pyridine, pyrazine, acridine, phenazine, benzofuran, benzothiophene, dibenzofuran, dibenzothiophene, benzoxazole, benzothiazole, thianthrene, phenoxazine, and phenothiazine which have an electron-accepting substituent, and condensed heterocyclic radicals which are condensed with a benzene ring or an aromatic condensed polycyclic group and assembled ring radicals constituted by direct combination of two or more of the heterocyclic monocyclic groups and the condensed heterocyclic polycyclic groups.

11. The electrophotographic photosensitive member of claim 1, wherein a subbing layer is provided between the electroconductive support and the photosensitive layer.

12. The electrophotographic photosensitive member of claim 1, wherein a protective layer is provided on the photosensitive layer.

13. An electrophotographic apparatus comprising an electrophotographic photosensitive member having a photosensitive layer on an electroconductive support, said photosensitive layer comprising a laminated structure of a charge-generating layer on the electroconductive support and a charge-transporting layer on the charge-generating layer, wherein said charge generating layer contains a dispersed compound having a structure represented by the general formula (1) or (2) as a charge-generating material.
wherein $A_1$ and $A_3$ are respectively an aromatic radical or an aromatic heterocyclic radical; wherein when $A_3$ is an electron accepting moiety, then $A_1$ is an electron donating moiety and when $A_3$ is an electron donating moiety, then $A_1$ is an electron accepting moiety; $A_2$ is hydrogen atom and n is an integer of 1, 2, or 3.

* * * * *

UNITED STATES PATENT AND TRADEMARK OFFICE
CERTIFICATE OF CORRECTION

PATENT NO. : 5,286,589
DATED : February 15, 1994
INVENTOR(S) : SHINTETSU GO, ET AL.

Page 1 of 4

It is certified that error appears in the above-indentified patent and that said Letters Patent is hereby corrected as shown below:

COLUMN 1

Line 26, "layer" (first occurrence) should read --layer)--.

COLUMN 2

Line 54, "dimethylamino," (second occurrence) should read --diethylamino,--.
Line 61, "(2)." should read --(2),-- and "moieties." should read --moieties,--.

COLUMN 3

Line 25, "dibenzotetrathiafluvalene," should read --dibenzotetrathiafulvalene,--.

COLUMN 4

Line 7, "iodine" should read --iodine;--.
Line 8, "radical:" should read --radical;--.
Line 37, "1976," should read --1976),--.
Line 57, "exhibits" should read --exhibit--.

COLUMN 35

Line 13, "support&" should read --support--.
Line 30, "from" should read --from a--.
Line 47, "haIogenated" should read --halogenated--.
Line 68, "anthracenne," should read --anthracene,--.

UNITED STATES PATENT AND TRADEMARK OFFICE
CERTIFICATE OF CORRECTION

PATENT NO. : 5,286,589
DATED : February 15, 1994
INVENTOR(S) : SHINTETSU GO, ET AL.

It is certified that error appears in the above-indentified patent and that said Letters Patent is hereby corrected as shown below:

COLUMN 36

Line 9, "compounds" should read --compounds,--.
Line 21, "includes" should read --include--.
Line 52, "eleotrophotographic" should read --electrophotographic--.

COLUMN 37

Line 29, "(no&" should read --(not--.
Line 30, "shown)" should read --shown),--.
Line 48, "be" should read --a--.
Line 61, "has" should read --was--.
Line 64, "end" should read --and--.

COLUMN 39

Line 36, "aluminum/pallium/arsine" should read --aluminum/gallium/arsine--.
Line 62, "−300 V" should read -- −700 V--.

COLUMN 40

Line 18, "compound (5 )" should read --compound (5g)--.

COLUMN 41

Line 4, "eIectrophotographic" should read --electrophotographic--.
Line 38, "charge generating" should read --charge-generating--.

UNITED STATES PATENT AND TRADEMARK OFFICE
CERTIFICATE OF CORRECTION

PATENT NO. : 5,286,589
DATED : February 15, 1994
INVENTOR(S) : SHINTETSU GO, ET AL.

Page 3 of 4

It is certified that error appears in the above-indentified patent and that said Letters Patent is hereby corrected as shown below:

COLUMN 42

Line 4, "radicaIs" should read --radicals--.
Line 6, "radicais" should read --radicals--.
Line 8, "heterocyciic" should read --heterocyclic--.
Line 10, "radicais." should read --radicals.--.
Line 25, "monocyciic" should read --monocyclic--.
Line 44, "a" should be deleted.

COLUMN 43

Line 3, "end" should read --and--.

COLUMN 44

Line 12, "group" should read --group;--.
Line 30, "charge generat-" should read --charge-generat- --.

UNITED STATES PATENT AND TRADEMARK OFFICE
CERTIFICATE OF CORRECTION

PATENT NO. : 5,286,589
DATED : February 15, 1994
INVENTOR(S) : SHINTETSU GO, ET AL.

It is certified that error appears in the above-indentified patent and that said Letters Patent is hereby corrected as shown below:

COLUMN 44

Line 33, "material." should read --material:

--.

Signed and Sealed this

Twenty-fifth Day of October, 1994

Attest:

BRUCE LEHMAN

Attesting Officer     Commissioner of Patents and Trademarks